(12) United States Patent
Reinhardt

(10) Patent No.: US 6,358,256 B1
(45) Date of Patent: Mar. 19, 2002

(54) APPARATUS FOR PULLING OUT AN OBJECT, HAVING AN ELONGATED INNER LUMEN, FROM ITS ANCHORAGE IN A BODY

(75) Inventor: Joerg Reinhardt, Grenzach-Wyhlen (DE)

(73) Assignee: VascoMed Institut fuer Kathetertechnologie GmbH, Weil am Rheim (DE)

(*) Notice: Subject to any disclaimer, the term of this patent is extended or adjusted under 35 U.S.C. 154(b) by 0 days.

(21) Appl. No.: 09/598,851

(22) Filed: Jun. 20, 2000

(30) Foreign Application Priority Data

Jun. 24, 1999 (DE) .......................................... 199 28 901

(51) Int. Cl.[7] .............................................. A61B 17/50

(52) U.S. Cl. ...................... 606/108; 607/126; 623/1.11; 623/11.11

(58) Field of Search ................................ 606/108–129, 606/32; 623/1.11, 11.11, 12.11; 604/96, 264; 607/122, 127, 128, 126

(56) References Cited

U.S. PATENT DOCUMENTS

| | | | | |
|---|---|---|---|---|
| 4,762,130 A | * | 8/1988 | Fogarty et al. | 604/96 |
| 5,279,299 A | * | 1/1994 | Imran | 607/126 |
| 5,344,439 A | * | 9/1994 | Otten | 607/126 |
| 5,632,749 A | | 5/1997 | Goode et al. | |
| 6,136,005 A | * | 10/2000 | Goode et al. | 606/108 |
| 6,159,219 A | * | 12/2000 | Ren | 606/108 |

* cited by examiner

Primary Examiner—Pedro Philogene
(74) Attorney, Agent, or Firm—Jordan and Hamburg LLP

(57) ABSTRACT

An extraction apparatus for heart pacemaker electrodes or defibrillator electrodes has an anchoring part which can be deformed using an actuating device from a displacement configuration into an expanded locking configuration. The anchoring part has a tube section with several wall cut-outs, which are offset in the axial direction and between which guide rings remain, which are connected by trough-shaped cross members. By exerting a tensile force on a control wire using the actuating device, the tube section is compressed and the trough-shaped cross members are deformed radially, so that they attain engagement with the inner lumen of the spiral helix of a heart pacemaker electrode cable or defibrillator electrode cable and, as a result of a spiral offset, bring about a positive locking, which permits high pull-out forces.

30 Claims, 4 Drawing Sheets

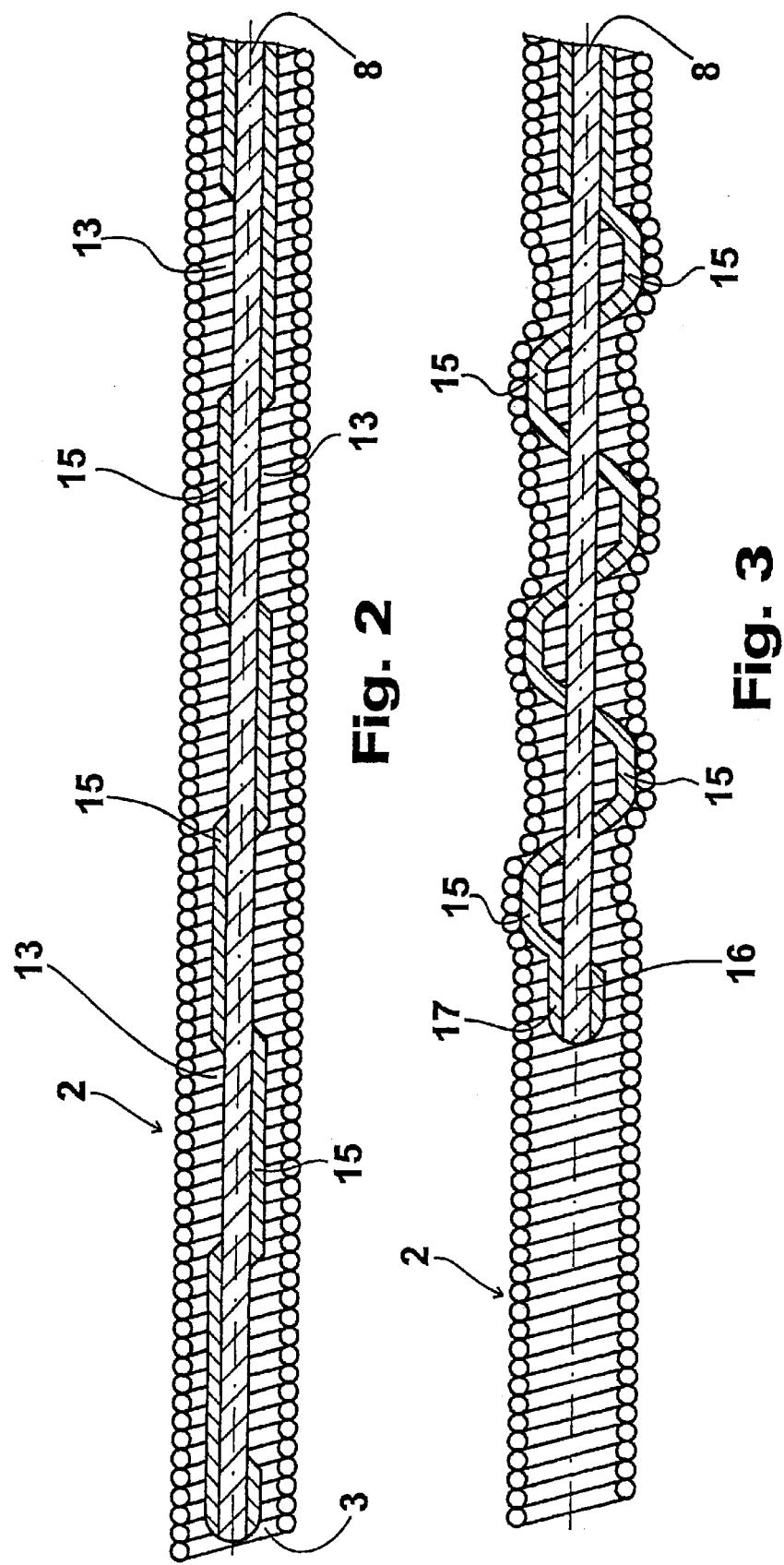

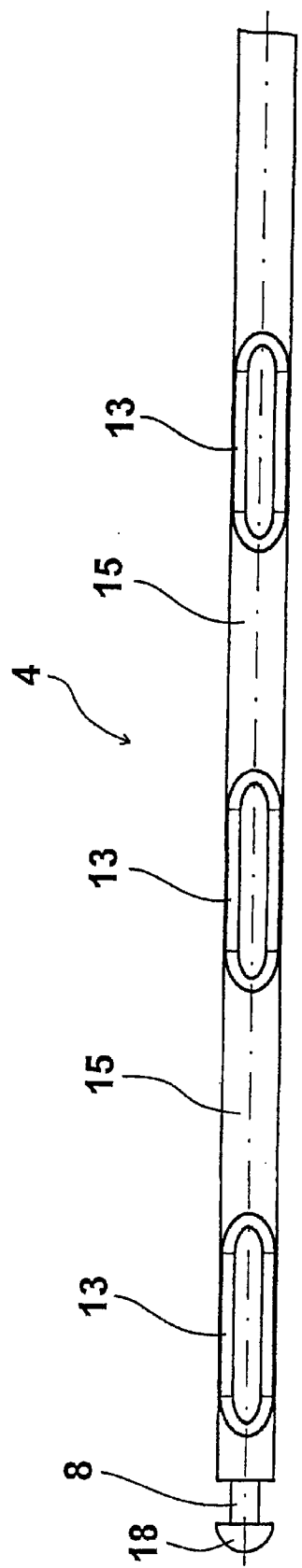
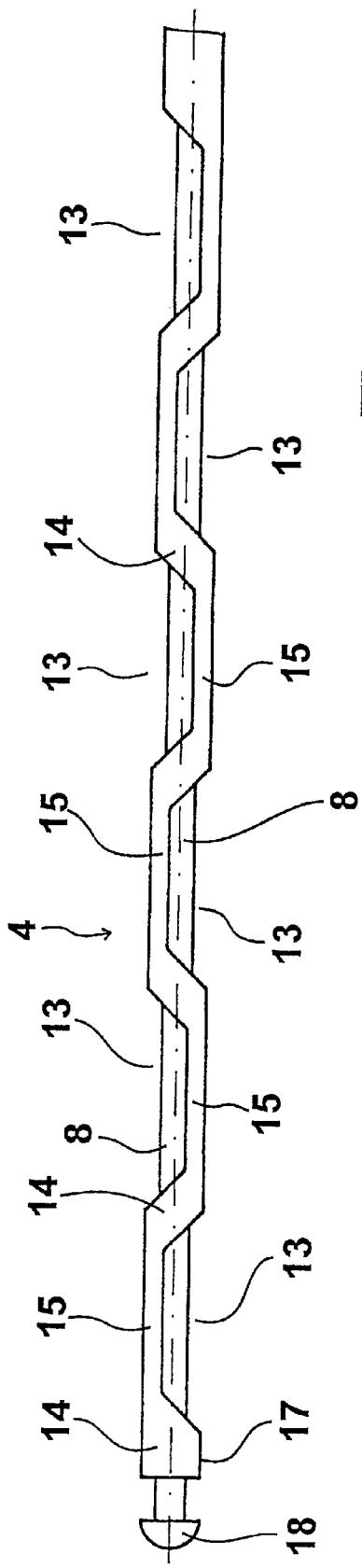
Fig. 4
Fig. 5

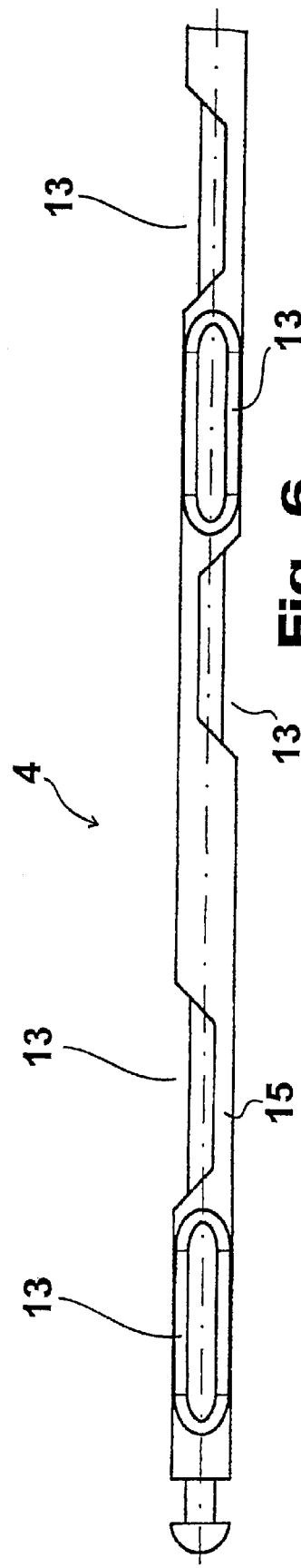
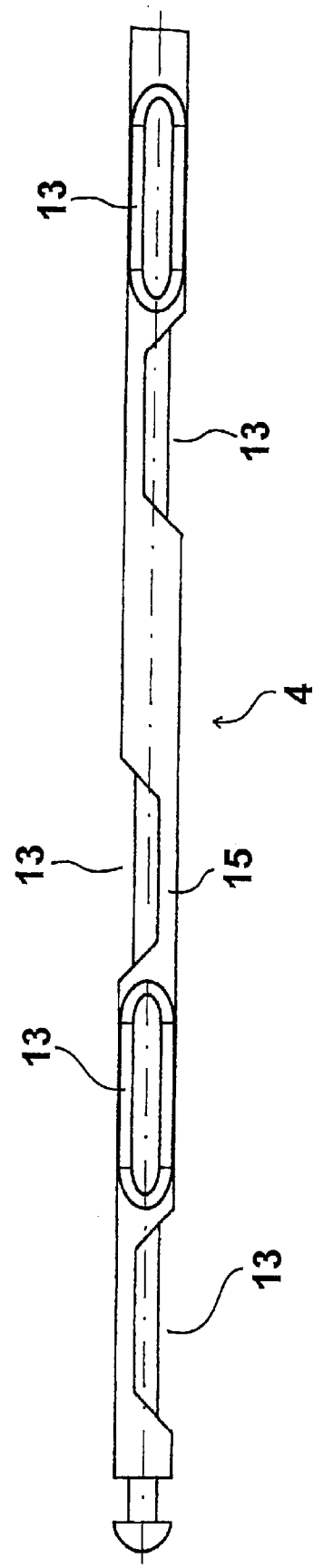

APPARATUS FOR PULLING OUT AN OBJECT, HAVING AN ELONGATED INNER LUMEN, FROM ITS ANCHORAGE IN A BODY

BACKGROUND OF THE INVENTION

The invention relates to an apparatus for pulling out an object, having an elongated inner lumen, from its anchorage in a body, particularly a heart pacemaker electrode or a defibrillator electrode with an electrode cable having a spiral helix. The apparatus has an anchoring part which is introduced into the inner lumen of the object and activated by an actuating device, and a tube, through which a control wire extends, which is connected to the actuating device. A relative movement between the tube and the control wire produces an axially acting force which deforms the anchoring part from a displacement configuration and to an expanded locking configuration to engage the lumen.

An apparatus is described in U.S. Pat. No. 5,632,749 which is one of the previously known embodiments and has an anchoring part constructed as a slotted sleeve, which can be activated by the relative movement between the tube and the control wire. The sleeve is slotted along its longitudinal axis and constructed in such a way that, for activating the apparatus, it can be enlarged in diameter. For this purpose, mutually facing conical surfaces are provided at the distal end of the tube as well as at the distal end of the control wire. These conical surfaces are brought into engagement with the slotted sleeve by pulling the control wire so that the slotted sleeve is expanded and, along a plurality of windings of a spiral helix, is pressed against spiral helix of an electrode cable, in order to achieve a frictional connection.

It is a disadvantage of this apparatus that, in order to achieve an adequate frictional connection, high axial forces must be exerted on the slotted sleeve pulling the control wire and holding the sleeve against the tube. It is a further disadvantage that only a relatively slight increase in the diameter of the slotted sleeve is possible. For this reason, differently dimensioned extraction devices must be kept in readiness, depending on the diameter of the inner lumen of the spiral helix of the heart pacemaker electrode or the defibrillator electrode.

A further extraction device, known from U.S. Pat. No. 5,632,749, has a flexible tube which, in the vicinity of its distal end, has several parallel divisions, which are distributed over the periphery of the flexible tube and extend axially. In this way, several strips, which are directly adjacent to one another in the circumferential direction, are formed between the divisions. The control wire of the extraction device, which is shown in FIG. 12 of U.S. Pat. No. 5,632,749, is connected with a distal end of the flexible tube. With one pull of the control wire, the front end of the flexible tube end is compressed and the strips, formed between the incisions, are deformed toward the outside and pressed against the spiral helix.

The pull-out forces achievable with this device are extremely slight, since the friction, achievable with the radially bulging strip, is limited to a very small contact area between the bulging strip and the spiral helix.

SUMMARY OF THE INVENTION

Starting out from the state of the art described above, it is an object of the invention to provide an extraction apparatus, especially an extraction apparatus for single spiral or multi-spiral heart pacemaker electrodes or defibrillator electrodes, which apparatus can be used relatively largely independently of a diameter of an inner lumen, and permits high pull-out forces to be transferred.

This objective is accomplished for an apparatus of the type described above because an anchoring part, in its locking configuration, has several radial expansions, which are offset relative to one another in the axial direction.

As a result of the radial expansions, which are offset to one another in the axial direction, a spiral helix forming a lumen is deformed by a spiral offset of adjacent spirals, so that, aside from a frictional connection between the anchoring part and the spiral helix, an interlocking connection is formed, which permits high pull-out forces. This effect is noticeable at low radial forces of the anchoring part particularly in the case of multi-spiral heart pacemaker electrodes or defibrillator electrodes.

In the case of a preferred embodiment, the anchoring part has a thin-walled metallic tube section which is provided with axially extending wall incisions, which are disposed at an axial distance from one another. Moreover, the wall incisions can be formed alternately on opposite sides of the wall of the tube. Alternatively, it is also possible for adjacent wall incisions, in the circumferential direction of the tube, to be disposed offset in each case by a quarter of the circumference of the tube.

The wall incisions can also be disposed so that easily deformable cross members remain in the radial direction between adjacent wall incisions. Moreover, the arrangement can be such that, in addition to the cross members, mutually offset in the axial direction, radially opposite cross members or several cross members along the circumferential direction, which are not offset from one another in the axial direction, are also provided.

The length of the wall incisions for producing cross members, which are or are not offset, is a multiple of the diameter of the tube, for example, three times the diameter of the tube.

The wall incisions can also be constructed as wider wall cut-outs. In particular, the wall cut-outs can extend so far into the tube casing or into the tube wall, that only a trough is left over from the original tube. If the height of this trough is significantly less than the radius of the tube, the deformability is particularly good.

In the case of an appropriate embodiment, provisions are made so that the wall cut-outs, at their axial ends, form an angle of about 30 degrees to 90 degrees and preferably of 45 degrees with the longitudinal axis of the tube.

In the case of a preferred embodiment, a distal end of the control wire is firmly connected with a distal end of the tube section forming the anchoring part. In this way, the tube section, forming the anchoring part, can be stressed not only in compression but also in tension for the purpose of deforming the anchoring part.

In the case of a different embodiment, the distal end of the control wire is provided with a stop head, which can come to rest against the distal end of the tube section forming the anchoring part. Alternatively, it is also possible to construct the distal end of the tube as a deformable tube section, which is connected in one piece with the tube, or to provide the anchoring part or the tube section as an independent part, separate or separable from the tube.

BRIEF DESCRIPTION OF THE DRAWINGS

In the following, embodiments of the invention are explained in greater detail by means of the drawings, in which:

FIG. 2 shows an anchoring part of the apparatus in an inner lumen of a spiral helix of an electrode cable in longitudinal section in a representation, enlarged compared to that of FIG. 1;

FIG. 3 shows a representation of the anchoring part, corresponding to that of FIG. 2, after this anchoring part has been transferred into a locking form and has produced several spiral offsets in the spiral helix of the electrode cable because of the deformation of the anchoring part;

FIG. 4 shows a plan view of an embodiment of the invention, modified from that of FIGS. 1 to 3, for which a stop head, which can be moved relative to the anchoring part, is provided;

FIG. 5 shows a side view of the anchoring part, shown in plan view in FIG. 4, together with a control wire, crossing the anchoring part, and with the stop head, which can be moved relative to the anchoring part;

FIG. 6 shows a representation, corresponding to that of FIG. 4, of a modified embodiment of the anchoring part, for which, in contrast to the representation of FIGS. 4 and 5, adjacent wall sections are offset to one another not by 180 degrees, but by 90 degrees; and FIG. 7 shows a representation, corresponding to that of FIG. 6, for which the anchoring part of FIG. 6 has been rotated by 90 degrees about its longitudinal axis.

DETAILED DESCRIPTION

Figure 1:
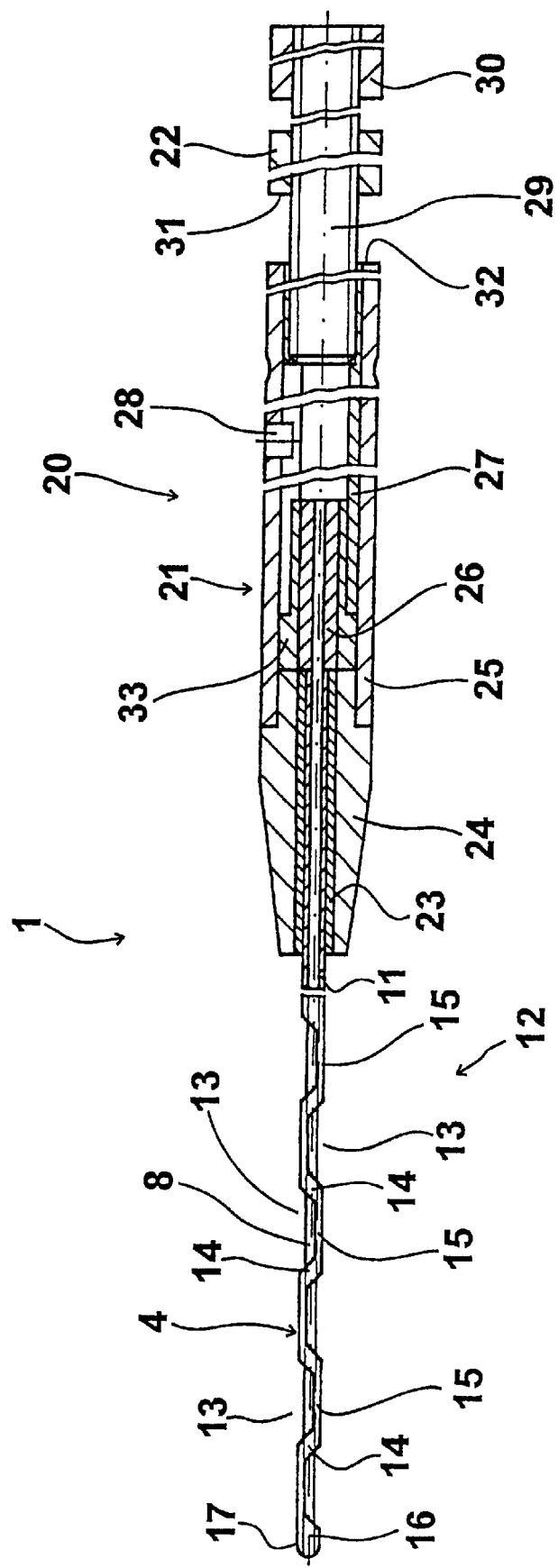
FIG. 1 shows an embodiment of the invention in the form of an apparatus for removing transvenously implanted heart pacemaker electrodes or defibrillator electrodes in a longitudinal section, a tube, protruding to the left out of an actuating device shown, being shown in a greatly shortened and truncated fashion.

An apparatus, shown in FIG. 1, for pulling out an object having an elongated inner lumen from its anchorage in a body is an extraction apparatus 1, produced preferably from a sterilizable metal, for removing transvenously implanted heart pacemaker electrodes or defibrillator electrodes, which are anchored with their distal end in the heart muscle of a patient. Such heart pacemaker electrodes or defibrillator electrodes are connected over an electrode cable with an assigned heart pacemaker or defibrillator.

The extraction apparatus I has an anchoring part 4, a control wire 8 and a tube 11, which is shown greatly shortened in the drawing and has a length of the order of 50 cm to 1 meter. The tube 11 has an external diameter of less than a millimeter, for example of 0.4 to 0.8 millimeter. The control wire 8 has a diameter of less than 0.5 millimeters for example, of 0.2 millimeter and is guided, sliding easily, in an interior of the tube 11.

In the case of the embodiment shown in FIG. 1, the anchoring part 4 has a tube section 12 formed at the distal end of the tube 11.

In a preferred embodiment of the invention, the length of the anchoring part is significantly shorter than the length of the object having the elongated inner lumen. However, it is also possible to provide a longer length for the anchoring part. In particular, the length of the anchoring part 4 may correspond to the length of the object having the inner lumen or may even be longer.

In the case of the embodiment shown in FIG. 1, the tube section 12 has six wall cut-outs 13. Tube segments, which remain between the wall cut-outs 13, form guide rings 14, between which the trough-shaped cross members 15 extend. In the case of the embodiment shown in FIG. 1, the trough-shaped cross members 15 are disposed alternately opposite to and at an axial distance from one another and have a length that is a multiple of the diameter of the tube 11, such as three times the diameter of the tube.

The control wire 8 extends through the guide rings 14 along the trough-shaped cross members 15 through the anchoring part 4 and the tube 11 and is firmly connected, in the case of the embodiment of the invention shown in FIG. 1, at its distal end 16 with the distal end 17 of the anchoring part 4. However, it can be moved freely with respect to the guide rings 14 and the trough-shaped cross members 15. For this reason, if the tube 11 is stationary, a pull at the control wire 8 compresses the anchoring part 4, deforming it and bringing about a locking conformation.

To produce the deformation, it is necessary to exert an axial force on the anchoring part 4 with the help of the control wire 8. The actuating device 20, intended for this purpose and shown on the right in FIG. 1, consists of a handle 21 for accommodating the tube 11 and an actuating sleeve 22 which, with the help of a threaded arrangement, permits a rotation to be converted with a rotary force into a tensile force exerted on the control wire 8, in order to activate and anchor the anchoring part 4, after it is introduced into the distal end of the spiral helix 2 of the heart pacemaker electrode cable or defibrillator electrode cable shown in FIG. 2.

The tube 11 extends through a tube-fastening sleeve 23, which in turn is fastened in a head 24 of the handle 21. The head 24 of the handle 21 is fastened to the distal end of a sleeve 25 of the handle 21. The proximal end of the tube 11 as well as the control wire 8 extend through the tube-fastening sleeve 23. The control wire 8 extends up to a wire fastening sleeve 26, which is firmly connected to the proximal end of the control wire 8 and, in turn, is fastened to a connecting piece 33.

In the interior of the sleeve 25 of the handle 21, the connecting piece 33, together with the control wire 8, is axially displaceable and firmly connected with the first end of an axially displaceable connecting sleeve 27. The connecting sleeve 27 is guided in the sleeve 25 of the handle and can be displaced axially. As a barrier to rotation, the connecting sleeve 27 has a longitudinal slot, which can be seen in FIG. 1 and into which a pin 28 protrudes.

At its second end, the connecting sleeve 27, which can be shifted in the longitudinal direction, is firmly connected with a grub screw 29, which protrudes out of the sleeve 25 of the handle 21. At its proximal end, the grub screw 29 has a connecting element 30, which may be provided with a transverse borehole for a traction cable.

By rotating the actuating sleeve 22, which is provided with an internal thread, on the grub screw 29, the face 31 of the actuating sleeve 22 can be pulled against the end surface 32 of the sleeve 25 of the handle 21 in order to exert very sensitively in this way a tensile force on the grub screw 29 and with that, on the connecting sleeve 27, the connecting piece 33, the wire-fastening sleeve 26 and, with that, the control wire 8.

Therefore, in order to active the extraction device shown in FIG. 1, is only necessary, after the anchoring part 4 is introduced into the spiral helix 2, which is shown without its casing in FIG. 2, to bring the actuating sleeve 22 into contact by rotating it against the sleeve 25 of the handle 21 and, by a further rotation, to bring about a shortening of the anchoring part 4.

FIG. 2 shows the anchoring part 4 in its displacement configuration, after it is introduced into the spiral helix 2.

FIG. 3, in a representation corresponding to that of FIG. 2, shows how, by shortening the anchoring part 4, the trough-shaped cross members 15 are deformed radially towards the outside under guidance by the guide rings 14 and, at the same time, are pressed against the inner wall of the spiral helix 2. Since the sides of the spiral helix 2, opposite to the cross member 15, are not exposed to a counter pressure, there is in each case a spiral displacement, which can be recognized clearly in FIG. 3, in the region of the trough-shaped cross members 15. The expansions of the trough-shaped cross members 15 in the axial direction accordingly lead not only to a frictional connection between the anchoring part 4 and the spiral helix 2, but also, at several places, to a spiral offset and, with that, to a positive locking. In the case of the embodiment shown in FIGS. 2 and 3, six wall cut-outs 13 and, with that, six trough-shaped cross members 15 are provided. Of course, the number of cross members 15 can be larger or smaller. The effect of the spiral offset to provide a secure fastening can be attained already with two trough-shaped cross members 15, shifted mutually in the axial direction.

As a result of the multiple deformations, which can be seen in FIG. 3 and are the outcome of a tensile force at the control wire 9, there is a very reliable anchoring which, as a consequence of positive locking, permits even high forces to be transferred in the case of spiral helixes with widely differing diameters.

If, in an unfavorable case, it is impossible to remove the electrode cable, then it is possible to make the anchoring part 4, shown in FIG. 3 in its locking configuration, more slender and to transfer it into displacing configuration corresponding approximately to the original configuration shown in FIG. 2, in that, as the tube 11 or the actuating device 20 is held fast, the actuating sleeve 22 is loosened and a pushing force, acting to the left in FIG. 3, is exerted on the control wire 9. The control wire 9 is firmly connected at its distal end 16 with the distal end 17 of the anchoring part 4. Therefore, when the control wire 8 is advanced after the anchoring part 4 is compressed, a tensile force is exerted, which extends the anchoring part 4 axially and, at the same time, reduces it in size radially. Alternatively, it is also possible, after the actuating sleeve 22 is loosened, simply to pull at the handle 21, so that, in the case of easily deformable trough-shaped cross member 15, a reversal of the deformation of the anchoring part 4 takes place, which permits the then extending anchoring part 4 to be pulled out.

FIGS. 4 and 5 show the distal end of an extraction device 1 with force transfer between the distal end of the control wire 8 and the distal end 17 of the anchoring part 4, which is different from the force transfer of the embodiment of FIGS. 1 to 3.

As can be seen in FIGS. 4 and 5, the control wire 8 crosses the anchoring part 4 and is guided in the latter axially movably by guide rings 14, which are connected with one another in each case by trough-shaped cross members 15. In the case of the embodiments shown in FIGS. 4 and 5, the guide ring 14, formed at the distal end 17 of the anchoring part 4 serves as a stop for a stop head 18, which is formed at the distal end of the control wire 8. The stop head 18 permits a tensile force to be exerted on the anchoring part 4 for the purpose of deforming the anchoring part. By means of this tensile force, the anchoring part 4 is transformed into the locking conformation corresponding to that of FIG. 3. Admittedly, for unlocking, a tensile force cannot be exerted with the help of the stop head 19. However, in the previously described manner, the actuating device can be unlocked and a reversal of deformation of the anchoring part 4 can be attained simply by pulling out.

As can be seen in FIGS. 4 and 5, the anchoring part 4, on its upper side shown in FIG. 4, has three wall cut-outs 13, which are formed at an axial distance from one another. There are also three wall cut-outs 13 on the opposite underside of the anchoring part 4 at an axial distance from one another in a regular arrangement, in that in each case the same distances and in each case the same offset of 180 degrees is provided between adjacent wall cut-outs 13. Instead of the opposite and regular arrangement, it is also possible to dispose the wall cut-outs 13 offset at an angle to one another and/or to have an irregular offset instead of a periodic offset.

FIGS. 6 and 7 show an anchoring part 4, for which adjacent wall cutouts 13 are disposed offset from one another at an angle of 90 degrees in the circumferential direction and not at an angle of 180 degrees. Angles other than 180 degrees and 90 degrees are also possible.

It can be seen in FIGS. 4 to 7 that the wall cut-outs 13 have a chamfering angle of about 45 degrees at their front and rear ends. Of course, bevels with a larger or smaller angle can also be used. In addition, it is seen that the wall cut-outs 13 have a constant depth in the central region, as a result of which trough-shaped cross members 15 with a constant cross-sectional shape are formed in this region. The deeper the penetration of the wall cut-outs 13 into the casing of the tube, the less is the height of the trough-shaped cross members 15 and, with that, the force required to deform the anchoring part 4 for the purpose of locking.

The described modifications of the anchoring part 4 in each case have trough-shaped cross members 15, to which no further cross members are assigned in the circumferential direction and, in particular, opposite. In the case of an embodiment, which is not shown in the drawing, the wall cut-outs 13 are formed by wall incisions of lesser width (in the extreme case, only a slot), so that there are several trough-shaped cross members in the circumferential direction. In the case of such an arrangement, there is also a positive connection because the radial expansions are offset from one another in the axial direction as a result of a spiral offset in the spiral helix 2 of the electrode cable. The positive connection permits a pulling-out force to be exerted, which is significantly higher than that, when there are only expansions, which are distributed over the circumferential direction and to which expansions, producing a spiral offset, are not assigned in the longitudinal direction.

What is claimed is:

1. An apparatus for pulling out an object, having an elongated inner lumen from its anchorage in a body, the apparatus comprising:

an anchoring part for introduction into the inner lumen of the object having radially expandable sections offset from one another and discrete in an axial direction of the anchoring part;

a tube having a control wire extending therethrough and through the anchoring part, an end of the tube engaging a base of the anchoring part and the control wire having a distal end engaging a distal end of the anchoring part; and an actuating device for effecting relative axial movement between the tube and the control wire to apply an axially acting force on the anchoring part to effect deformation of the anchoring part between a displacement configuration and an expanded locking configuration, wherein the anchoring part has in the locking configuration the radially expandable section expanded in the radial direction and offset from one another.

2. The apparatus of claim 1, wherein the anchoring part is a tube section having axially extending wall incisions which are disposed at an axial distance from one another and define the radially expandable sections.

3. The apparatus of claim 2, wherein the wall incisions are formed alternately on radially opposite sides of a tube wall of the tube section.

4. The apparatus of claim 2, wherein adjacent ones of the wall incisions are offset in a circumferential direction of a circumference of the tube from one another.

5. The apparatus of one of the claims 2 to 4, wherein the radially expandable sections are deformable cross members defined in the radial direction between opposing sides of the wall incisions.

6. The apparatus of one of the claims 2 to 4, wherein the length of the wall incisions in a multiple about three times a diameter of the tube section.

7. The apparatus of one of the claims 2 to 4, wherein the wall incisions are formed as wall cut-outs.

8. The apparatus of claim 7, wherein, in a central region of the wall cut-outs, the wall of the tube section is removed to form the radially expandable sections in a trough shape.

9. The apparatus of claim 8, wherein the wall cut-outs form at axial ends thereof an angle of about 30 degrees to 90 degrees with respect to a longitudinal axis of the tube section.

10. The apparatus of one of the claims 2 to 4, wherein the distal end of the control wire is firmly connected to the distal end of the tube section which is the distal end of the anchoring part.

11. The apparatus of one of the claims 2 to 4, wherein the distal end of the control wire has a top head contacts against the distal end of the tube section which is the distal end of the anchoring part to effect engagement thereof.

12. The apparatus of one of the claims 2 to 4, wherein the distal end of the tube section is constructed as a deformable tube section.

13. The apparatus of one of the claims 1 to 4, wherein anchoring part is separable from the tube.

14. The apparatus of one of the claims 1 to 4, wherein the anchoring part has a lenght which is shorter than a length of the object having the elongated inner lumen.

15. The apparatus of one of the claims 1 to 4, wherein the anchoring part has a lenght which corresponds approximately to the length of the object having the inner lumen.

16. The apparatus of one of the claims 1 to 4, wherein the anchoring part has a lenght which is longer than the length of the object having the elongated inner lumen.

17. An apparatus for engaging an inner lumen of an object, the apparatus comprising:
   an anchoring part for introduction into the inner lumen of the object, said anchoring part defining an axis and having a base end and a distal end, said anchoring part including:
      ring sections disposed along said axis and displaced axially from each other, ones of said ring sections being respective disposed at said base end and said distal end; and
      interconnecting sections, single ones of said interconnecting sections being disposed between and interconnecting adjacent ones of said ring sections, said interconnecting sections thereby being separated from one another by said ring sections in an axial direction of said anchoring part, said interconnecting sections being deformable away from said axis in a radial direction by compressive force applied said ring sections in said axial direction;
   a tube having a control wire extending therethrough and through said anchoring part, an end of said tube engaging said base end of said anchoring part and said control wire having a distal end engaging said distal end of said anchoring part; and
   an actuating device for effecting relative axial movement between said tube and said control wire to apply an axially acting compressive force on said anchoring part to effect said deformation of said interconnecting sections by compressive force applied by said ring sections in said axial direction.

18. The apparatus of claim 17 wherein said base end is integral with said tube.

19. The apparatus of claim 18, wherein said interconnecting sections are successively axially disposed alternately on radially opposite sides of said axis of said anchoring part.

20. The apparatus of claim 18, wherein said interconnecting sections are successively axially disposed radially offset from adjacent ones thereof.

21. The apparatus of claim 17, wherein said interconnecting sections are successively axially disposed alternately on radially opposite sides of said axis of said anchoring part.

22. The apparatus of claim 17, wherein said interconnecting sections are successively axially disposed radially offset from adjacent ones thereof.

23. The apparatus of one of the claims 17, 21 or 22, wherein a length of said interconnecting section is a multiple about three times a diameter of said ring sections.

24. The apparatus of claim 17, wherein said interconnecting sections have a trough shape with a concave surface directed to said axis.

25. The apparatus s of claim 17, wherein said ring section have edges joining said interconnecting sections and disposed at an angle in a range of about 30 degrees to about 90 degrees with respect to said axis of said anchoring part.

26. The apparatus of claim 17, wherein said ring section have edges joining said interconnecting sections and disposed at an angle of about 30 degrees with respect to said axis of said anchoring part.

27. The apparatus of claim 17, wherein said ring section have edges joining said interconnecting sections and disposed at an angle of about 90 degrees with respect to said axis of said anchoring part.

28. The apparatus of the claim 17, wherein said distal end of said control wire is fixed to said distal end of said anchoring part.

29. The apparatus of claim 17, wherein said distal end of said control wire has a stop head contacting against said distal end said anchoring part to effect engagement thereof.

30. The apparatus of the claim 17, wherein said anchoring part is separable from said tube.

\* \* \* \* \*